United States Patent [19]
Batina et al.

[11] Patent Number: 4,562,840
[45] Date of Patent: Jan. 7, 1986

[54] TELEMETRY SYSTEM

[75] Inventors: William P. Batina; Lamar H. Gipson, both of Miami, Fla.

[73] Assignee: Cordis Corporation, Miami, Fla.

[21] Appl. No.: 592,517

[22] Filed: Mar. 23, 1984

[51] Int. Cl.$^4$ .............................................. N61N 1/00
[52] U.S. Cl. ............................... 128/419 PT; 128/903
[58] Field of Search ....... 128/419 P, 419 PS, 419 PT, 128/696, 697, 702, 708, 903, 631

[56] References Cited
U.S. PATENT DOCUMENTS

| | | | |
|---|---|---|---|
| 3,195,540 | 7/1965 | Waller | 128/419 PG |
| 3,426,748 | 2/1969 | Bowers | 128/419 PT |
| 3,580,243 | 5/1971 | Johnson | 128/696 |
| 4,000,461 | 12/1976 | Barber et al. | 128/708 |
| 4,223,679 | 9/1980 | Schulman et al. | 128/419 PT |
| 4,252,129 | 2/1981 | Tamora et al. | 128/903 |

OTHER PUBLICATIONS

Furman et al., "Medical Research Engineering" 3rd Qtr., 1967, pp. 29–32.

*Primary Examiner*—William E. Kamm
*Attorney, Agent, or Firm*—George H. Gerstman

[57] ABSTRACT

A telemetry system is provided for communicating with an implanted pacer. A patient's coil is positioned on the patient substantially overlying the implanted pacer. An FM oscillator generates a waveform which varies in frequency and amplitude in response to the telemetry signals from the implanted pacer. The varying frequency generated by the oscillator may be utilized to determine the proximity of the patient's coil with respect to the implanted pacer. An analog signal is generated that has a parameter which varies in inverse proportion to the proximity of the coil to the pacer. The varying waveform generated by the oscillator may also be used to reconstruct telemetry signals that are generated by a tank circuit that is contained in the pacer. An automatic gain control circuit is used to provide a corrected gain notwithstanding the position of the patient's coil with respect to the implant.

9 Claims, 10 Drawing Figures

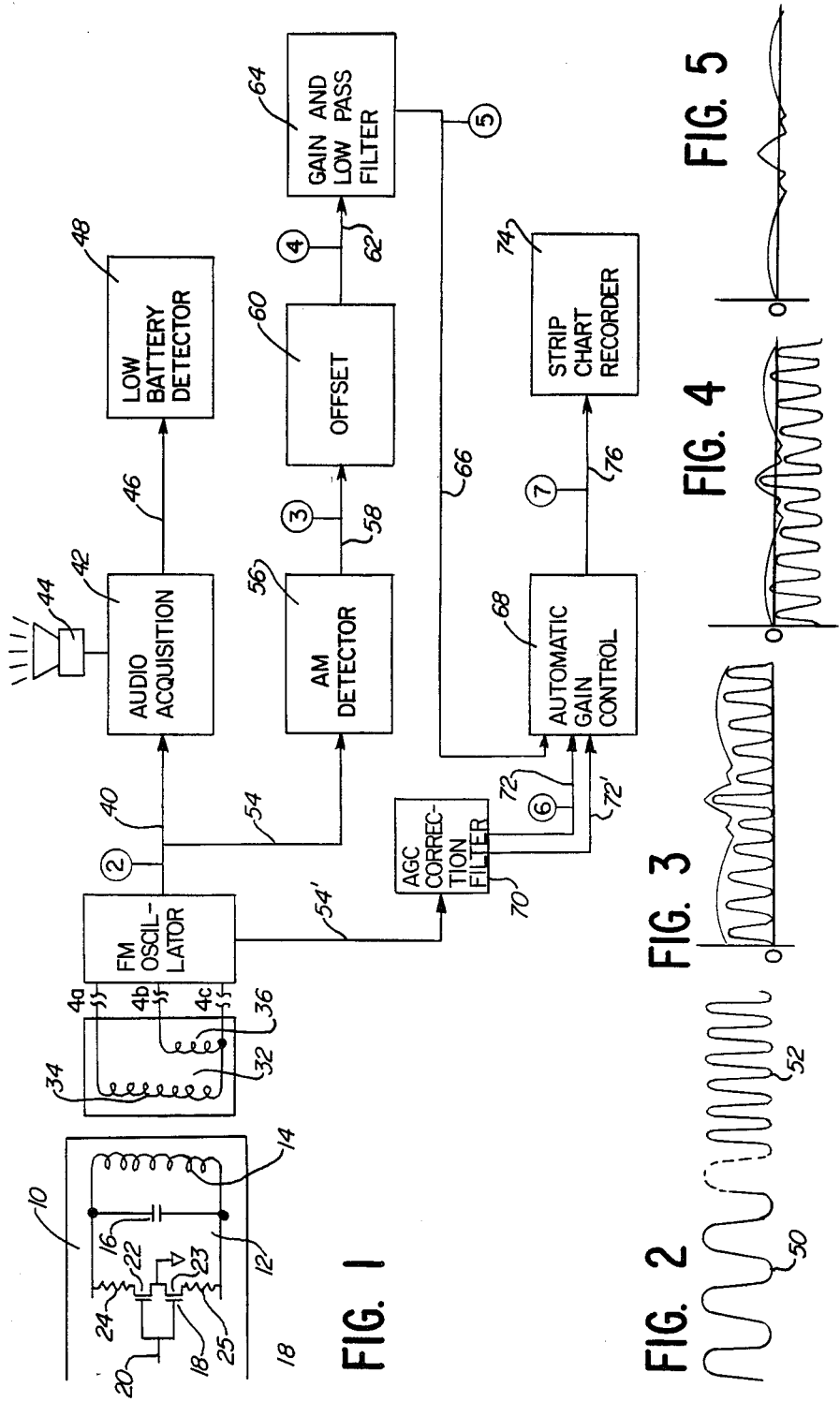

TELEMETRY SYSTEM

BACKGROUND OF THE INVENTION

The present invention concerns novel telemetry system for communicating with a pacer that is implanted within a patent.

In U.S. Pat. No. 4,361,153, issued Nov. 30, 1982 and assigned to the assignee of the present invention, there is disclosed the use of a resonant impedance modulated transponder, in a device implanted in the patient, to modulate the phase of a reflected magnetic signal that is the product of a magnetic carrier imposed from outside of the body. In this manner, information is transmitted from a fixed internal implant to a positionable external telemetry unit. A relatively high energy magnetic field at a carrier frequency is established by a transmitter in the external unit. The field permeates the skin, underlying tissue and case of the implant and induces a signal in a resonant, impedance modulated transponder in the implant tuned to the carrier frequency. A second field is reradiated or reflected at the carrier frequency by the resonant transponder. The transponder's impedance is varied in accordance with a modulation input signal, causing a shift in the phase angle and amplitude of the transponder's contribution to the composite reflected signal, thereby resulting in a proportional phase and amplitude shift in the composite reflected signal. The composite reflected signal is picked up and demodulated by a phase shift detector in the external telemetry unit.

We have discovered a different system for providing communication between the device implanted in the patient and the external telemetry unit. While the system disclosed in U.S. Pat. No. 4,361,153 typically utilizes a center coil which is driven by a fixed frequency oscillator with a pair of two outer coils picking up the carrier which is phase shifted by the pacer, the system we have discovered is simpler in that it may utilize a relatively simple coil that is actually separated from the circuitry in the external telemetry unit. Thus utilizing our discovery, a separate patient's coil, which is lightweight, can be positioned externally on the patient substantially overlying an implanted pacer, and a housing containing the other components of the external telemetry unit may be separated from the patient's coil. Further, our invention has the advantage that it requires relatively few components, it is simple to manufacture, and is easy to operate.

In Schulman et al. U.S. Pat. No. 4,223,679, a telemetry system is disclosed in which an externally located oscillator is controlled by impedance changes in an impedance reflecting circuit located in an implanted pacer. We have discovered that the oscillator-controlled type of telemetry system can be improved upon significantly. For example, we have discovered that the oscillator output can be arranged to provide detection of the proximity of the patient's coil in our system using an analog varying signal having a parameter which varies in inverse proportion to the proximity of the patient's coil to the pacer. This enables the operator to determine when the patient's coil is in the proper position overlying the implanted pacer. We have also discovered the use of an automatic gain control circuit for correcting the gain from the oscillator output notwithstanding varying locations of the patient's coil with respect to the pacer. This enables the chart recording of the telemetered signal to be accurate and consistent.

Other advantages of the present invention will become apparent as the description proceeds.

SUMMARY OF THE INVENTION

In accordance with the present invention, a telemetry system is provided for communicating with a tank circuit contained in an enclosure implanted in a patient. The system comprises a patient's coil for positioning externally on the patient, substantially overlying the implanted enclosure. An oscillator is connected to the patient's coil and capacitive means are connected to the patient's coil and the oscillator. The capacitive means and the patient's coil form a resonant tank which sets the frequency of the oscillator. The oscillator with the resonant tank are operative for generating a waveform that varies in both frequency and amplitude in response to the telemetry signals from the implanted tank circuit. The waveform generated by the oscillator is detected in order to detect the telemetry signals.

In the illustrative embodiment, the oscillator and the detecting means are enclosed within a housing and the patient's coil is separated from the housing by a flexible lead.

In the illustrative embodiment, the oscillator is an FM oscillator and the detector means comprises an AM detector coupled to the output of the FM oscillator. An offsetting gain circuit is coupled to the output of the AM detector and a low pass filter is coupled to the output of the offsetting gain circuit. An automatic gain control circuit is coupled to the output of the low pass filter. An automatic gain control voltage correction filter for receiving the DC representation of the distance of the patient coil relative to the implant is provided. The automatic gain control circuit also is coupled to the output of the voltage correction filter.

In accordance with the present invention, a process is provided for communicating with an implanted pacer, which comprises the steps of positioning a patient's coil on the patient substantially overlying the implanted pacer, generating a waveform which varies in frequency and amplitude in response to telemetry signals from the implanted pacer, and detecting the waveform generated, whereby the telemetry signals are detected.

In one embodiment of the invention, a system is provided for detecting the proximity of an external telemetry and/or programming unit with respect to an implanted pacer. To this end, the oscillator described above is operative to generate a waveform that varies in frequency in response to the proximity of the external telemetry and/or programming unit with respect to the implanted pacer. The output of the oscillator is coupled to means for providing an analog varying signal indicating the proximity of the unit, such as audio means which vary in pitch in response to proximity.

A more detailed explanation of the invention is provided in the following description and claims, and is illustrated in the accompanying drawings.

BRIEF DESCRIPTION OF THE DRAWINGS

FIG. 1 is a block diagram of a telemetry system constructed in accordance with the principles of the present invention.

FIG. 2 illustrates a waveform present on one of the lines of the FIG. 1 system;

FIG. 3 illustrates a waveform present on another line of the system of FIG. 1;

FIG. 4 illustrates a waveform present on another line of the FIG. 1 system;

FIG. 5 illustrates a waveform present on another line of the FIG. 1 system;

FIG. 6 illustrates a waveform present on another line of the FIG. 1 system;

FIG. 7 illustrates a waveform present on another line of the FIG. 1 system; and

DETAILED DESCRIPTION OF THE ILLUSTRATIVE EMBODIMENT

Figure 8A:
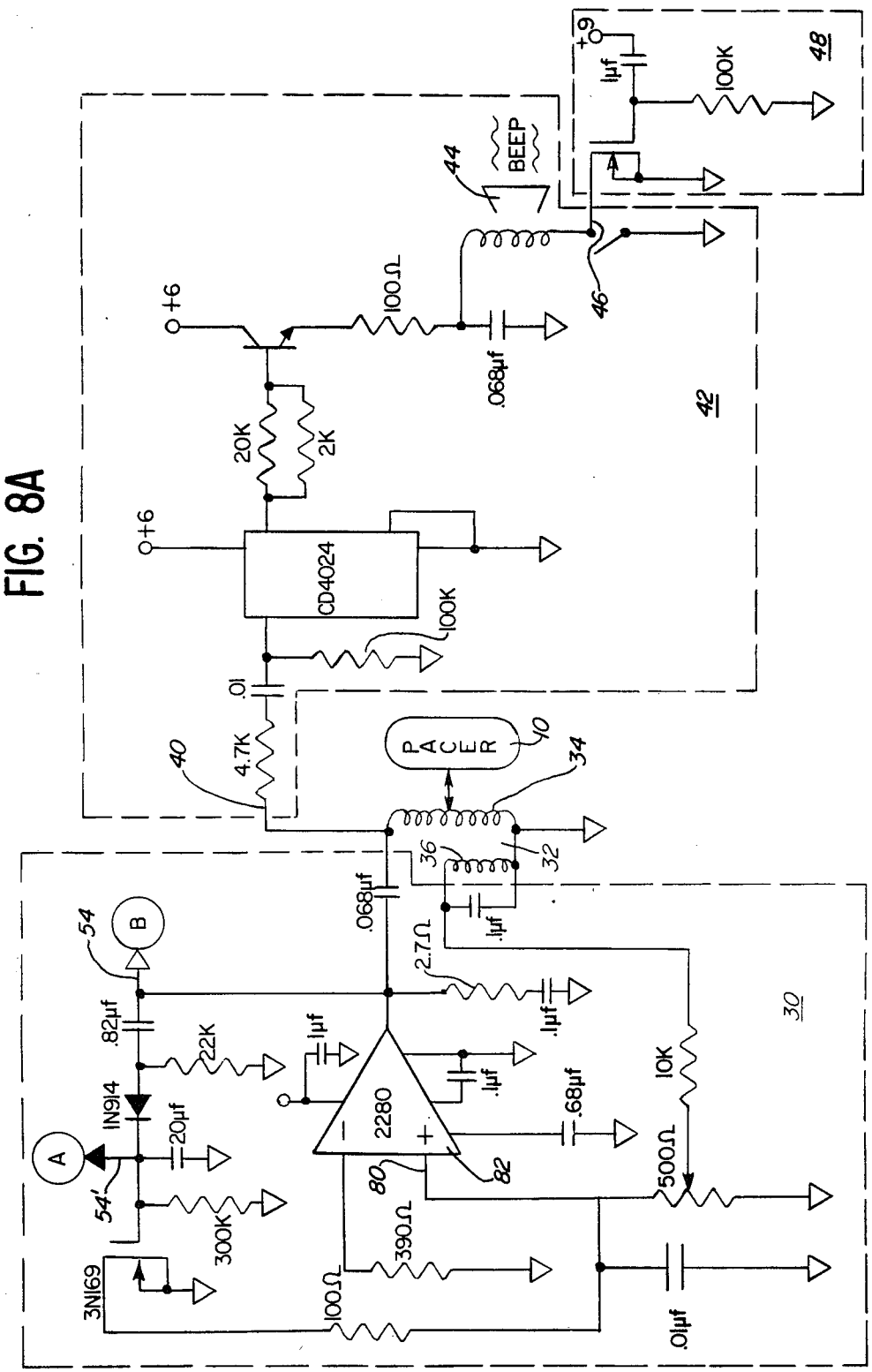
FIGS. 8a, 8b and 8c, when connected together, form a schematic circuit diagram of the telemetry system of FIG. 1.

Referring to FIG. 1, an implant 10 is shown therein, including a tank circuit 12 comprising a tuned coil 14, a capacitor 16, and a shunt circuit 18 for varying the impedance of tank circuit 12 in accordance with an input data signal on line 20. Line 20 is connected to the common gates of a pair of FETs 22, 23, the sources of which are connected to the ground of implant 10 and the drains of which are connected, respectively, to resistors 24 and 25.

An external programming and telemetry unit includes, among other things, an FM oscillator 30. The FM oscillator has a patient's coil 32, comprising a primary 34 and a secondary 36. The patient's coil 32, is wire coupled via flexible leads 4a, 4b, 4c to the oscillator 30 and the rest of the external unit. In this manner, the patient's coil can be small and lightweight, and can be separated from the rest of the external unit by means of the wire, thereby allowing the patient's coil to be placed in a desired location overlying the implanted enclosure 10, with the remainder of the external unit separated therefrom.

Oscillator 30 is coupled via line 40 to audio acquisition circuit 42, which is connected to a speaker 44. Audio acquisition circuit 42 is coupled via line 46 to a low battery detector 48.

In accordance with the present invention, oscillator 30 will provide a varying frequency in response to the positioning of coil 32 relative to coil 14 of implant 10. Referring to FIG. 2, the waveform from oscillator 30 is shown therein with the first portion of the waveform having a particular frequency corresponding to the frequency generated by oscillator 30 when the patient's coil 32 is not in proximity to coil 14 of the implant 10. However, as patient's coil 32 approaches coil 14, the frequency will increase and portion 52 of the waveform of FIG. 2 illustrates the increased frequency waveform that is generated as a result of patient's coil 32 overlying the implant 10 and being in proximity with coil 14. Audio acquisition circuit 42, which receives this waveform, will indicate proximity of coil 32 with respect to coil 14 by issuing a sound from speaker 44 that is higher in pitch as proximity is increased. Other analog varying proximity indicia, such as the increased illumination of an LED or a light bulb, sound amplitude, or rate of clicks, may alternatively be utilized. The indicia is provided in inverse proportion to the proximity. The proportion is non-linear, and the sound or light amplitude increases as there is closer proximity, the pitch increases as there is closer proximity, the rate of the clicks increases as there is closer proximity, etc.

Low battery detector 48, which is coupled to audio acquisition circuit 42, enables the operator or patient to determine if the battery in the external programming unit is too low for proper operation.

The FIG. 2 waveform generated by FM oscillator 30 is fed via line 54 to an AM detector 56 which cuts the carrier wave in half to effectively save the top half of the carrier wave. The output of AM detector 56 is illustrated in FIG. 3. This output is fed via line 58 to an offsetting gain circuit 60 which strips off the DC that is inherently developed by the AM detector. The output of offsetting gain circuit 60 is illustrated in FIG. 4. This output is fed via line 62 to a gain and low pass filter circuit 64 which is tuned to a cut off frequency of, for example, 250 hertz. The output of low pass filter 64 is illustrated in FIG. 5. This enables the message to be recovered from the waveform, and this message is fed via line 66 to automatic gain control circuit 68. Also fed to the automatic gain control circuit 68 is the DC representation 54' of the distance of the patient coil 32 relative to coil 14. That signal passes through the automatic gain control voltage correction filter 70 and is fed via line 72, 72' to automatic gain control circuit 68. The output of automatic gain control voltage correction filter 70 on line 72, 72' is illustrated in FIG. 6.

The purpose of using automatic gain control circuit 68 is so that a strip chart recorder 74, which is coupled via line 76 to the output of the gain control circuit 68, will have a corrected gain notwithstanding the particular position of the patient coil 32 with respect to implant 10. Otherwise, if patient coil 32 was at different distances, strip chart recorder 74 would receive different amplitude signals and operate erratically. The output of automatic gain control circuit 68, which is on line 76, is illustrated in FIG. 7, and it is this output which drives strip chart recorder 74 to provide a graphical recordation of the data signals. Strip chart recorder 74 may have an output jack for connecting the strip chart recorder to a telephone line for transmitting the message via telephone to a physician.

For additional information concerning the implanted tank circuit 12 and its telemetry operation, reference is hereby made to U.S. Pat. No. 4,361,153. Although the telemetry operation has been described, it is to be understood that this system may be used for programming. To this end, oscillator 30 would transmit carrier pulses instead of a continuous carrier signal. The carrier pulses would be outputted in response to programmed control by a microprocessor and the implant 10 would carry means for receiving and storing the program that is transmitted by the oscillator under the control of the microprocessor.

Figure 8B:
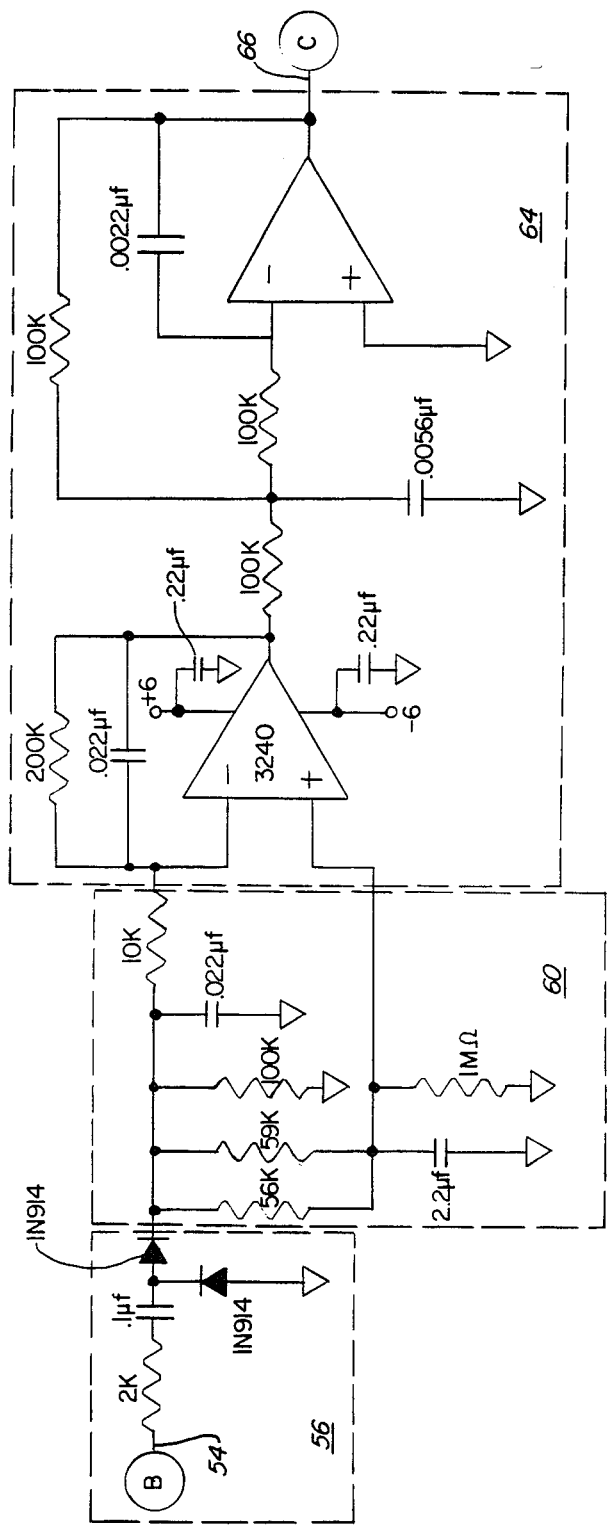
Figure 8C:
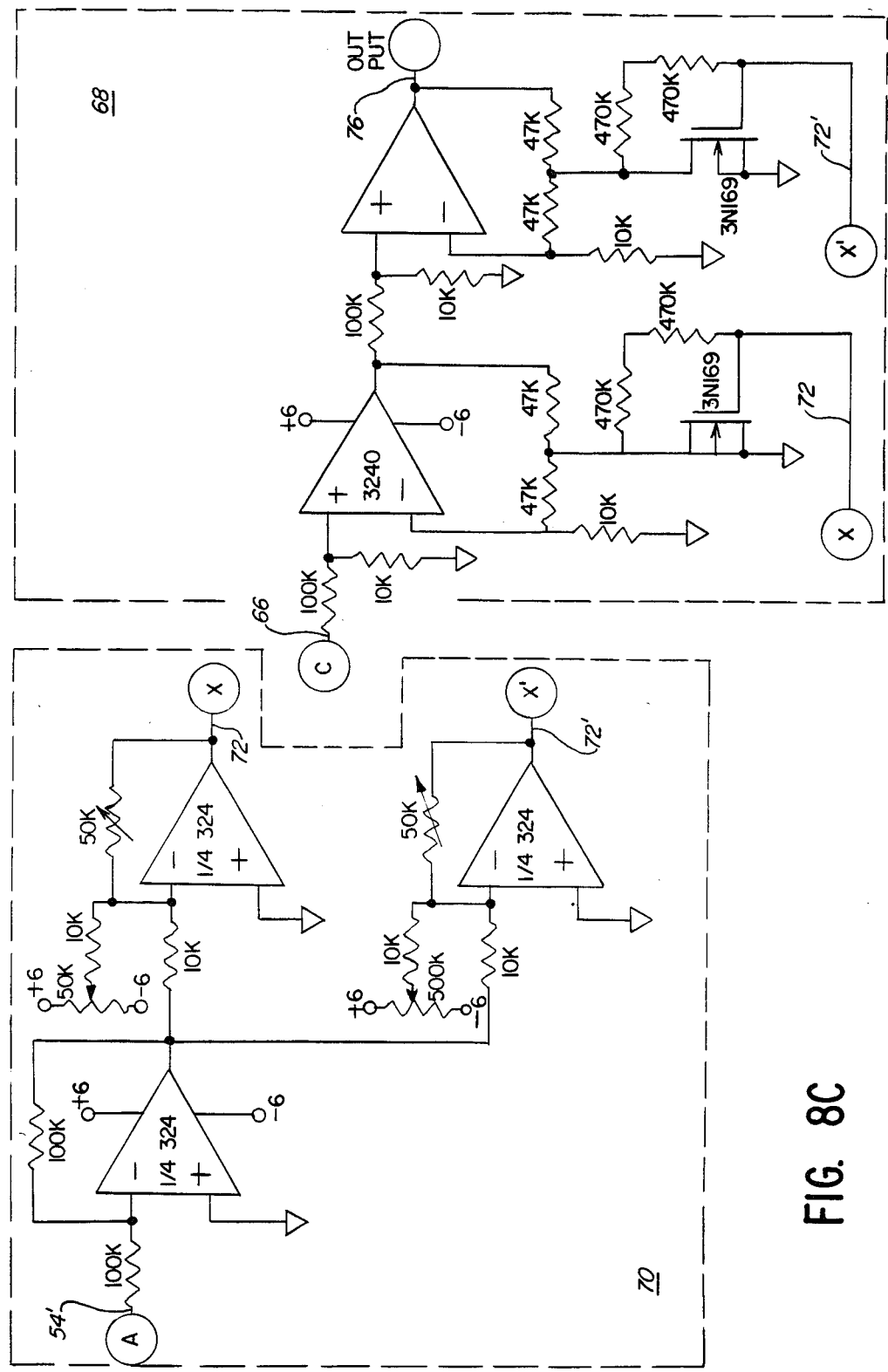

While a block diagram of the various circuits is illustrated in FIG. 1, in FIGS. 8a to 8c an example of circuits which may be used is illustrated in schematic form. Referring to FIG. 8a, FM oscillator 30, coupled to audio acquisition circuit 42 via line 40 is shown therein. The reference numerals for the circuit items illustrated in FIG. 1 are used in FIGS. 8a to 8c. In FIG. 8a it can be seen that patient coil 32 comprises primary 34 and secondary 36, with the secondary 36 being fed back to the non-inverting terminal 80 of operational amplifier 82 and with the primary 34 acting as a transmission coil with respect to implanted pacer 10.

In FIG. 8a, low battery detector circuit 48 is illustrated as being coupled to audio acquisition circuit 42 via line 46.

Referring to FIG. 8b, AM detector circuit 56 is illustrated as being coupled to offset circuit 60 which is coupled to gain and low pass filter 64. Output line 66 illustrated in FIG. 8b is coupled to input C of automatic gain control circuit 68 (FIG. 8c). Referring further to FIG. 8c, it is seen that output lines 72 and 72' of automatic gain control voltage correction filter 70 are connected to inputs of automatic gain control circuit 68, the output of automatic gain control circuit 68 being represented by a reference numeral 76. As stated above, output 76 may be coupled to a conventional strip chart recorder, which is not part of the external programming and telemetry unit but is typically a separate connected unit.

The circuit illustrated in FIGS. 8a-8c may be utilized with a 16 kilohertz normal carrier frequency generated by oscillator 30. However, it is to be understood that the circuitry illustrated in FIGS. 8a and 8b is an example, and other equivalent circuits may be utilized.

The frequency and the amplitude of the carrier on line 40 and line 54 will be responsive to the telemetry signals generated by the implanted tank circuit 12. The carrier frequency generated by oscillator 30 will also be responsive to the proximity of coil 34 to coil 14. Thus, as the impedance of the tank circuit 12 varies in response to the telemetry signals on line 20, this varying impedance will cause a variation in the frequency and the amplitude of the generated carrier signal from oscillator 30, which is detected and recorded.

Although an illustrative embodiment of the invention has been shown and described, it is to be understood that various modifications and substitutions may be made by those skilled in the art without departing from the novel spirit and scope of the present invention.

What is claimed is:

1. A telemetry system for communicating with a tank circuit contained in an enclosure implanted in a patient, which comprises:
    a patient's coil for positioning externally on the patient substantially overlying the implanted enclosure;
    a varying frequency FM oscillator connected to said patient's coil;
    capacitive means connected to said patient's coil and said varying frequency oscillator, with said capacitive means and said patient's coil forming a resonant tank which sets the frequency of said oscillator;
    said oscillator with said resonant tank being connected for generating a varying frequency and amplitude waveform in response to telemetry signals from the implanted tank circuit;
    means for detecting the waveform generated by said oscillator, whereby the telemetry signals are detected;
    said detector means comprising an AM detector coupled to the output of the FM oscillator, said AM detector providing a dc representation of the distance of the patient's coil to the implanted enclosure;
    an offsetting gain circuit to the output of the AM detector for stripping off said dc representation;
    a low pass filter coupled to the output of the offsetting gain circuit,
    an automatic gain control circuit coupled to the output of the low pass filter to provide a corrected gain notwithstanding the position of the patient's coil to the implanted enclosure; and
    output means coupled to the output of the automatic gain control circuit for displaying the communicated message.

2. A telemetry system as described in claim 1, including an automatic gain control voltage correction filter for receiving the DC representation of the distance of the patient coil to the implant coil; said automatic gain control circuit also being coupled to the output of the automatic gain control voltage correction filter.

3. A telemetry system as described in claim 1, including means coupled to the output of the automatic gain control circuit for recording the telemetered message.

4. A telemetry system for communicating with a tank circuit contained in an enclosure implanted in a patient which comprises:
    a patient's coil for positioning externally on the patient substantially overlying the implanted enclosure;
    a varying frequency oscillator connected to said patient's coil;
    capacitive means connected to said patient's coil and said varying frequency oscillator, with said capacitive means and said patient's coil forming a resonant tank which sets the frequency of said oscillator;
    said oscillator with said resonant tank being connected for generating a waveform that varies in frequency and amplitude in response to the telemetry signals from the implanted tank circuit;
    said oscillator comprising an FM oscillator;
    means for detecting the waveform generated by said oscillator, whereby the tendency signals are detected;
    said detector means comprising an AM detector coupled to the output of the FM oscillator, said AM detector providing a dc representation of the distance of the patient's coil to the implanted enclosure; an offsetting gain circuit coupled to the output of the AM detector for stripping off said dc representation; a low pass filter coupled to the output of the offsetting gain circuit; and an automatic gain control circuit coupled to the output of the low pass filter to provide a corrected gain notwithstanding the position of the patient's coil to the implanted enclosure;
    an automatic gain control voltage correction filter for receiving the DC representation of the distance of the patient coil to the implant coil; said automatic gain control circuit also being coupled to the output of the automatic gain control voltage correction filter; and
    recording means coupled to the output of the automatic gain control circuit.

5. A telemetry system as described in claim 4, including means for driving said oscillator for transmitting carrier pulses to the implanted tank circuit.

6. In a telemetry system for pacing in which an enclosure containing a data modulated tank circuit is implanted in a patient and a telemetry unit in a housing is used external of the patient, the improvement comprising, in combination:
    a patient's coil for positioning externally on the patient substantially overlying the implanted enclosure;
    a varying frequency FM oscillator located within said housing and connected to the patient's coil;
    capacitive means connected to said patient's coil and located within said housing, said capacitive means being connected to said varying frequency oscillator and forming a resonant tank which sets the frequency of said oscillator;
    said oscillator with said resonant tank being connected for generating a varying frequency waveform in response to telemetry signals from the implanted tank circuit;

means located in said housing for detecting the waveform generated by said oscillator, whereby the telemetry signals are detected;

said detector means comprises an AM detector coupled to the output of the FM oscillator, said AM detector providing a dc representation of the distance of the patient's coil to the implanted enclosure;

an offsetting gain circuit coupled to the output of the AM detector for stripping off said dc representation;

a low pass filter coupled to the output of the offsetting gain circuit;

an automatic gain control circuit coupled to the output of the low pass filter to provide a corrected gain notwithstanding the position of the patient's coil to the implanted enclosure; and output means coupled to the output of the automatic gain control circuit for displaying the communicated message.

7. In a telemetry system as described in claim 6, including an automatic gain control voltage correction filter for receiving the DC representation of the distance of the patient coil to the implant coil; said automatic gain control circuit also being coupled to the output of the automatic gain control voltage correction filter.

8. A system for detecting proximity of an external unit with respect to an implanted pacer, which comprises:

a patient's coil for positioning externally on the patient overlying the implanted pacer;

a varying frequency oscillator connected to said patient's coil;

capacitive means connected to said patient's coil and said varying frequency oscillator, with said capacitive means and said patient's coil forming a resonant tank which sets the frequency of said oscillator;

said oscillator with said resonant tank being connected for generating a varying frequency in response to proximity of the patient's coil to the implanted pacer; and means coupled to the output of said oscillator for providing a an audio tone which varies in inverse proportion to the proximity of the patient's coil to the implanted pacer.

9. A system as described in claim 8, in which said oscillator is an FM oscillator and said audio tone comprises an analog varying sound.

* * * * *